United States Patent [19]

Ellis et al.

[11] 4,077,397
[45] Mar. 7, 1978

[54] DIAGNOSTIC ELECTRODE ASSEMBLY

[75] Inventors: William Garrettson Ellis, Northfield, Ill.; Paul William Heavner, Jr., Kettering; Charles W. Daugherty, Xenia, both of Ohio

[73] Assignee: Baxter Travenol Laboratories, Inc., Deerfield, Ill.

[21] Appl. No.: 670,403

[22] Filed: Mar. 25, 1976

Related U.S. Application Data

[63] Continuation of Ser. No. 512,588, Oct. 7, 1974, abandoned.

[51] Int. Cl.² .............................................. A61B 5/04
[52] U.S. Cl. ............................. 128/2.06 E; 128/2.1 E; 128/417; 128/DIG. 4
[58] Field of Search ............ 128/2.06 E, 2.1 E, 172.1, 128/404, 405, 410, 411, 416, 417, 418, DIG. 4

[56] References Cited

U.S. PATENT DOCUMENTS

| | | | |
|---|---|---|---|
| 3,187,745 | 6/1965 | Baum et al. ...................... | 128/2.06 E |
| 3,685,645 | 8/1972 | Kawaguchi ......................... | 128/417 |
| 3,701,346 | 10/1972 | Patrick et al. ...................... | 128/2.1 E |
| 3,788,317 | 1/1974 | McCormick ....................... | 128/2.06 E |
| 3,828,766 | 8/1974 | Krasnow ............................ | 128/2.1 E |
| 3,834,373 | 9/1974 | Sato ................................... | 128/2.1 E |
| 3,865,099 | 2/1975 | Robicheud ......................... | 128/2.1 E |
| 3,882,853 | 5/1975 | Gofman et al. ................... | 128/2.06 E |
| 3,901,218 | 8/1975 | Buchatter ......................... | 128/2.06 E |

*Primary Examiner*—Dalton L. Truluck
*Assistant Examiner*—Lee S. Cohen
*Attorney, Agent, or Firm*—Eugene M. Cummings; Paul C. Flattery; John P. Kirby, Jr.

[57] ABSTRACT

A disposable electrode assembly for establishing electrical contact with an underlying skin surface includes a relatively thin base member having a central hub portion and an adhesive-coated undersurface, a conductive gel-impregnated sponge contact contained in a downwardly facing recess located in the hub, and a relatively thick and inflexible cover member coextensive with the base member. In storage the cover member is attached to the undersurface of the base member by the adhesive and the sponge is confined within the recess. Prior to use the base member is peeled away from the cover member to expose the adhesive surface, which when applied to a skin surface holds the sponge contact in compression-contact therewith. A thumb recess is provided along the margin of the cover member to facilitate removal of the cover member.

5 Claims, 5 Drawing Figures

U.S. Patent March 7, 1978 4,077,397
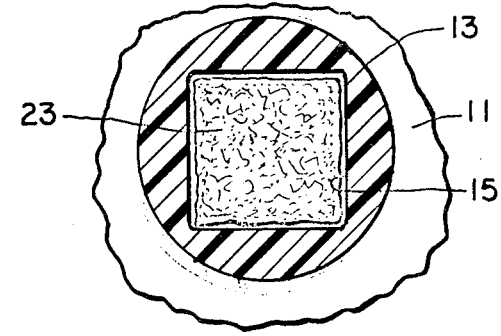
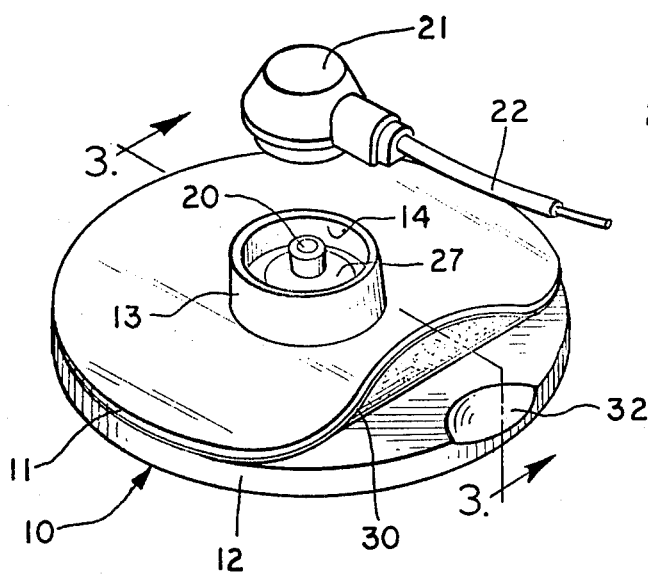
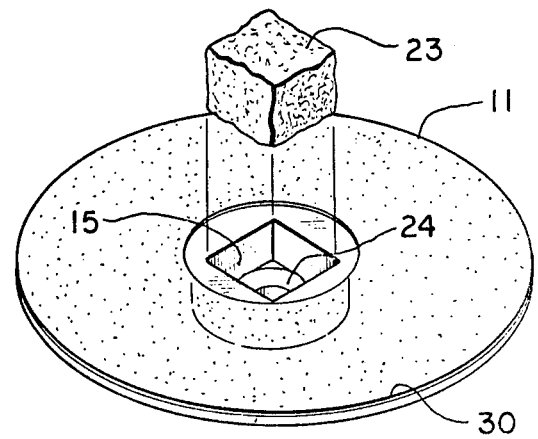
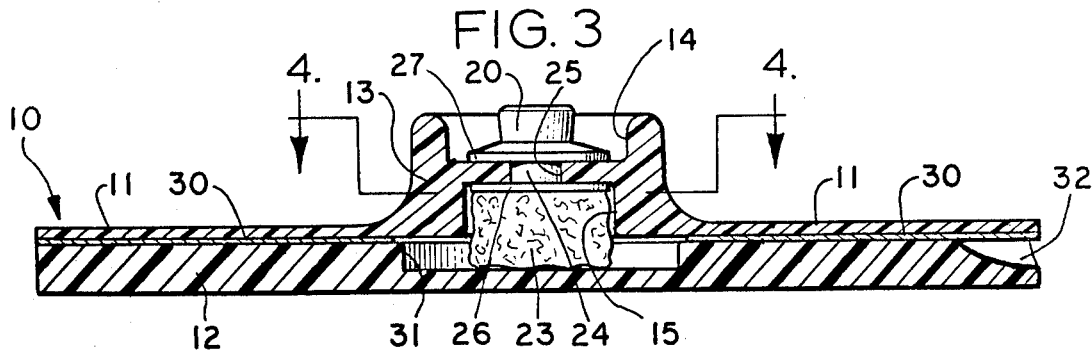
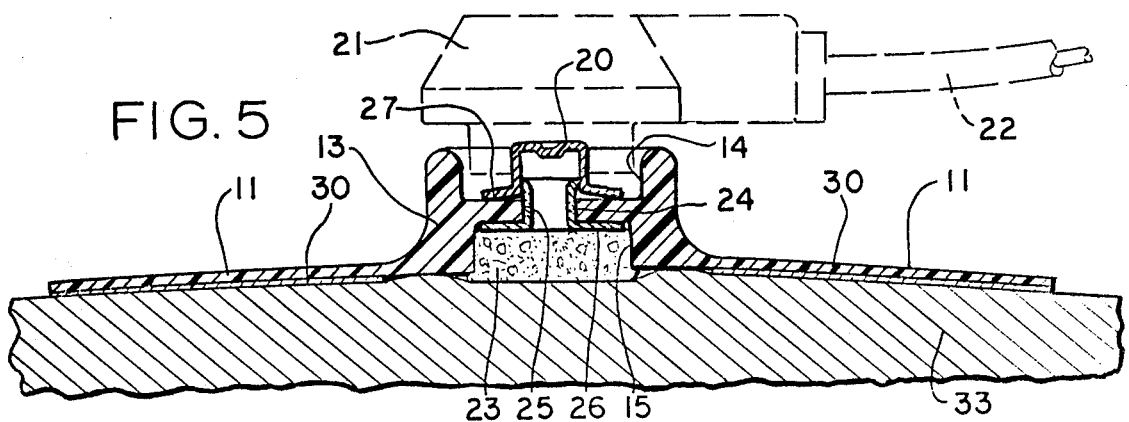

DIAGNOSTIC ELECTRODE ASSEMBLY

This is a continuation of application Ser. No. 512,588, filed Oct. 7, 1974, now abandoned.

BACKGROUND OF THE INVENTION

The present invention relates generally to disposable electrodes, and more particularly to a skin contact electrode assembly for detecting cardiac and other low level electrical signals generated within the human body.

Skin contact electrodes find extensive use for detecting and transforming potentials generated within the body into electrical signals which may be monitored for a variety of functions, such as the preparation of electrocardiograms and electroencephalograms. Originally, such electrodes were of the permanent or non-disposable type wherein a metal electrode was placed in contact with the skin with an interposed layer of electrolyte, generally in gel form. Not only was the placing of the electrode, which often had to be strapped to the patient, cumbersome and inconvenient, but the application of the gel electrolyte had to be done very carefully to avoid contact with the clothes of the patient and the person conducting the test. In addition, the electrodes had to be cleaned after each use for reasons of sanitation and to insure a good electrical contact.

In recent years, with the advent of portable and more sophisticated EKG and other types of biomedical monitoring equipment, disposable electrode assemblies, wherein the metallic electrode and the electrolyte gel, together with an adhesive for holding the electrode in position, are combined in a unitary assembly for one-time use, have come into wide use. Not only do these assemblies avoid the time-consuming processes of applying gel and strapping the electrode in position, but they also avoid the necessity of cleaning the electrode after each use.

Unfortunately, prior art disposable type electrode assemblies have not been entirely satisfactory in all respects. Typically, such electrode assemblies have used thin paper or plastic adhesive-backed base members to which the electrode was attached, and a cover member for covering the adhesive until ready for use. Because the base and cover members provided little or no stiffness to the assemblies, the assemblies were difficult to store and difficult to prepare for use. Furthermore, the elements of the assembly were often torn or damaged in attempting to remove the cover member prior to use, and the user was often subjected to undesired contact with either the electrolyte gel or the adhesive.

The lack of stiffness in prior art electrode assemblies also precluded stacking of the assemblies while in storage, making it necessary to package each assembly in an individually sealed package suitable for storage in a drawer or open box. This not only unnecessarily consumed the time of the user by requiring him to unwrap each package separately prior to use, but also unnecessarily increased the cost of the electrode assemblies. Attempts at placing more than one electrode assembly in a package proved unsatisfactory because the number of electrodes required for a particular situation varied, resulting in the unwrapping and discarding of unneeded electrodes. Accordingly, the need has developed for a disposable electrode assembly which can be conveniently stored and dispensed in a desired quantity with no waste or damage to unused electrodes.

Those assemblies which utilized a thicker or stiffer base member in attempting to overcome these difficiencies tended to separate from the skin after a period of time, and often caused discomfort to the patient during extended monitoring periods. Use of a stronger adhesive to hold the stiffer base members in position aggravated the discomfort of the patient as the electrodes were removed or repositioned. The use of a stiffer base member in prior art electrode assemblies also increased the possibility of spurious output signals being produced as the patient moved. Such motion artifacts resulted from mechanical disturbance of the electrolyte relative to the metal eletrode, which was aggravated by the use of a stiff base member above the skin contact area.

In addition to the aforementioned attributes of convenience of storage and use, it is necessary that a body electrode assembly of the disposable type be economical to manufacture and package. To this end the materials employed in its manufacture must be readily obtainable and the individual components utilized in the assembly must be capable of fabrication by efficient technique and processes. It is to a new and improved disposable electrode assembly which combines the desired economy of construction and convenience of packaging with low contact resistance, good adhesion and low motion artifacts, that the present invention is directed.

SUMMARY OF THE INVENTION

The invention is directed to a disposable electrode assembly for establishing an electrical connection to an adjacent skin surface. The electrode assembly includes a relatively flat thin base member formed of electrically non-conductive material and having an outside surface and an inside surface, and a raised center portion on the outside surface including a first recess forming a first open-ended chamber on the outside surface and a second recess forming a second open-ended chamber on the inside surface. Means comprising an electrically conductive terminal having an upper portion in the first chamber and a lower portion in the second chamber are included for establishing an electrically conductive path therebetween, the upper portion being adapted to receive a connecting terminal, and means comprising a sponge-like contact member saturated with electrically conductive fluid disposed within the second chamber are included for establishing an electrically conductive path between the lower portion of the terminal and the adjacent skin surface. The assembly further includes a relatively thick cover member which preferably is also relatively stiff having an inside surface substantially coextensive with the base member and being, overall, thicker than the base member and including a thumb recess along its margin to facilitate peeling the base member away therefrom, and means comprising an adhesive layer on the inside surface of the housing for holding the inside surface of the cover member against the inside surface of the base member when the electrode assembly is in storage, the base member being peelable away from the cover member to expose the inside surface of the base member for application to the skin surface, the adhesive holding the base member against the adjacent skin surface to enable the sponge-like contact member to establish electrical contact therewith.

BRIEF DESCRIPTION OF THE DRAWINGS

The features of the present invention, which are believed to be novel, are set forth with particularly in the appended claims. The invention, together with the further objects and advantages thereof, may best be understood by reference to the following description taken in connection with the accompanying drawings, in the several figures of which like reference numerals identify like elements, in which:

FIG. 1 is a perspective view of an electrode assembly constructed in accordance with the invention showing the base member partially peeled away from the backing member and showing a mating electrical contact for establishing electrical contact with the assembly.

FIG. 2 is a perspective view of the electrode assembly inverted showing the sponge-like skin contact member of the assembly removed from its recess in the inside face of the base element of the assembly.

FIG. 3 is a cross-sectional view taken along lines 3—3 of FIG. 1 showing the cover element of the electrode assembly in position for storage.

FIG. 4 is an enlarged cross-sectional view taken along lines 4—4 of FIG. 3 showing the raised or hub portion of the base member of the assembly.

FIG. 5 is a cross-sectional view of the electrode assembly showing the assembly in position on an underlying skin surface with a mating electrical connector shown in phantom.

DESCRIPTION OF THE PREFERRED EMBODIMENT

Referring to the figures, and particularly to FIGS. 1-3, an electrode assembly 10 incorporating the features of the present invention is seen to comprise a relatively thin flexible disc-shaped base member 11 formed or molded of a transparent non-conducting material such as plastic, and a relatively thick and inflexible disc-shaped cover member 12 of like diameter formed or molded of an opaque plastic material. The top (FIG. 1) or outside surface of the base includes a central raised or hub portion 13 which includes an upwardly-facing open-ended recess or chamber 14, and the bottom or inside surface of the base includes a four-sided downwardly-facing open-ended recess or chamber 15.

To facilitate electrical connection to an associated monitoring apparatus, an electrical snap-type connector terminal 20 is provided within chamber 14. This terminal, which may be of conventional design and construction, includes a slightly tapered upwardly-extending cylindrical portion which engages complementarily dimensioned inwardly-biased downwardly-extending contact fingers (not shown) on a female connector 21, which also may be conventional in design and construction. The effect of the open-ended chamber 14 is to form a socket or wall around terminal 20 which helps to prevent inadvertent disengagement of connector 21 from terminal 20, and inadvertent contact by the user with the electrical circuit established through the connector and the consequent erroneous output signals which might result from such contact. Connector 21 is connected by an insulated conductor 22 of appropriate length to the monitoring apparatus.

Electrical contact is made to the patient's skin by means of a compressible body contact member 23, which may be fabricated from a sponge-like material impregnated with an electrically conductive gel. While contact member 23 can be formed in various shapes and dimensions, it is preferably sized to fit within and occupy substantially the entire inside volume of chamber 15 to achieve the largest possible skin contact area for the lowest possible contact resistance. To this same end, the vertical dimension (in FIGS. 3 and 5) of contact member 23 is preferably such that the contact member is under compression when the inside surface of base 11 is pressed against the skin surface, as shown in FIG. 5.

An electrical connection is established between body contact member 23 and terminal 20 by means of a rivet-shaped electrically conductive retaining member 24 which extends between the rear wall of chamber 15 and the bottom of terminal 20. The retaining member 24 extends through an aperture 25 provided in base 11 between chamber 15 and chamber 14, and into a locking press-fit engagment with terminal 20. A flange portion 26 at the bottom end (as viewed in FIGS. 3 and 5) of member 24 prevents the member from being pulled through aperture 25 and provides increased contact area for establishing a low resistance electrical connection with body contact 23. A similar flange portion 27 on contact 20 prevents that member from being pulled through aperture 25, so that once members 20 and 24 have been press-fit together during manufacture of the electrode assembly a very secure electrically-integral attachment between the contacts and base 11 is obtained.

Referring to FIG. 3, while being stored prior to use the disc-shaped cover plate 12 overlies the interior surface of base 11 and is attached thereto by means of an adhesive layer 30, which preferably comprises an acrylic-based adhesive of a type which does not promote allergic reactions or irritation to the skin. This adhesive is deposited on both sides of a thin transparent disc-shaped polyethylene carrier or barrier which is provided with a central aperture so as not to overlie the open end of chamber 15. The adhesive layer 30 is sandwiched between the interior surface of base 11 and cover 12 to hold the two elements together, and cover member 12 is preferably provided with an open-ended chamber or recess 31 on its inside surface to allow partial expansion of the sponge-like skin contact 23 during storage. This enables the sponge to retain a greater quantity to conductive gel during storage, and consequently to release a greater amount of gel onto the underlying skin surface when compressed prior to use.

Prior to applying the electrode assembly 10 to a skin surface, the thin flexible and transparent base member 11 is peeled away from the relatively stiff cover member 12 to expose the adhesive surface, as shown in FIG. 1. To facilitate removal of the cover member a thumb recess 32 may be provided along the circumferential margin of cover 12. Since the cover is formed of thicker and less flexible material than the base 11, peeling the base member away from the backing member can be readily accomplished once the cover is initially separated by means of recess 32.

After the cover 12 has been removed the electrode assembly can be applied by pressing the inside surface of the base member 11 to the skin surface 33, as shown in FIG. 5. This compresses the sponge-like skin contact member 23 and releases conductive gel onto the underlying skin area, thereby establishing a low-resistance electrical connection through member 23 to the skin surface. The adhesive layer 30, which is substantially coextensive with the interior surface of base 11, adheres to the skin to hold the electrode assembly in position. To accomplish this the area of the adhesive 30 on the interior surface of base 11, and hence the diameter of the base, must be sufficiently large to obtain an adequate adhesive force, taking into consideration that the adherence of the adhesive to the skin must not be so great as to cause unnecessary discomfort to the patient when the electrode assembly is removed.

In a preferred embodiment of the invention the base member 11 is preferably fabricated of a transparent flexible polymer plastic or a suitable rubber-like material. One material which has proven successful for this application is polyvinyl chloride. In one exemplary embodiment the base member 11 may have an overall diameter of 2.5 inches, a skirt thickness of 0.021 inch, and a recess of 0.125 inch depth and 0.46 inch diameter.

The cover member 12 may be formed of a hydrophilic material such as polyethylene and may have color added to color code the electrode during storage. Typically, cover member 12 may have a thickness of approximately 0.125 inch, except under recess 31 wherein it may have a typical thickness of approximately 0.05 inch. In the exemplary embodiment the cover member preferably has a diameter of 2.532 inches and a recess having a diameter of 0.687 inch and depth of 0.075 inch. The sponge-like skin contact 23 may be formed of a polyether polyurethane foam impregnated with an ionic fluid in a suitable organic based gel, for example, that currently available from Parker Laboratories, Inc. under the trademark Spectra 360 or that available from Pharmacuetical Innovations, Inc. under the trademark LECTRON II, although other conductive fluids or gels may be used without departing from at least the broader principles of the present invention.

To reduce the attraction between the gel-impregnated contact member 23 and cover 12 as the base 11 is peeled away, the base is preferably formed of a material which is more hydrophilic than the cover. This is believed to cause the gel-impregnated sponge to be attracted to the base to greater extent than it is attracted to the cover, and therefore to tend to remain with the base. The snap terminal 20 and retaining member 24 are preferably formed of silver, silver-coated brass, brass, rhodium-coated brass, nickel, zinc-coated brass or stainless steel, although other conductors may be employed. Silver is preferred because it has the lowest half cell potential and therefore generates the least spurious signal with relative motion of contacts 20 and 21 as the patient moves.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

For example, although a sponge is preferred for the compressible body contact member 23, it is also possible to use other known alternatives, such as conductive gels which may be applied at the time of use. Also, other types of adhesive layers may be used, such as a single layer of adhesive without a carrier.

We claim:

1. A disposable electrode assembly for establishing an electrical connection to an underlying skin surface comprising, in combination:

a relatively flexible base member formed of electrically-insulating material having an outside surface and an inside surface;

contact means on said base member for establishing electrical contact with said underlying skin surface, said contact means including a first contact portion on said outside surface and a second contact portion in electrical communication with said first contact portion on said inside surface;

a cover member having an inside surface substantially coextensive with said inside surface of said base member, said cover member being, overall, substantially less flexible than the major extent of said base member and including a thumb recess along its margin at the inside surface to facilitate peeling said base member away therefrom; and an adhesive layer on the inside surface of said base member holding said inside surface of said cover member against said inside surface of said base member so as to increase the rigidity of said electrode assembly during storage, said base member being peelable away from said cover member to enable said adhesive layer to be placed in contact with the underlying skin surface to hold said second contact portion in contact with the skin surface while the electrode assembly is in use.

2. A disposable electrode assembly for establishing an electrical connection to an underlying skin surface comprising, in combination:

a base member formed of electrically-insulating material having an outside surface and an inside surface;

said base member including a raised hub portion on said outside surface and a relatively flexible flange portion surrounding said hub portion, said hub portion including a recess forming an open-ended chamber on said inside surface, and a connecting aperture extending from said chamber to said outside surface;

means comprising an electrically conductive terminal having a first portion on said outside surface, a second portion in said open-ended chamber, and a third portion extending through said connecting aperture, said first portion being adapted to receive a connecting terminal;

means comprising a sponge-like contact member saturated with electrically conductive fluid disposed within said chamber in contact with said second portion of said terminal for establishing an electrically conductive path between said terminal and said adjacent skin surface;

a cover member having an inside surface substantially coextensive with said inside surface of said base member, said cover member being, overall, substantially less flexible than said flange portion of said base member and including a thumb recess along its margin at the inside surface to facilitate peeling said base member away therefrom; and an adhesive layer on the inside surface of said base member holding said inside surface of said cover member against said inside surface of said base member so as to enclose said sponge-like contact member within said open-ended chamber and increase the rigidity of said electrode assembly during storage, said base member being peelable away from said cover member to enable said adhesive layer to be placed in contact with the underlying skin surface to hold said sponge-like contact member in contact with the skin while the electrode assembly is in use.

3. A disposable electrode assembly for establishing an electrical connection to an underlying skin surface comprising, in combination:

a relatively flexible disc-shaped base member formed of electrically-insulating material having an outside surface and a flat inside surface;

said base member including a raised center hub portion on said outside surface and a relatively flexible flange portion surrounding said hub portion, said hub portion including a first recess forming a first open-ended chamber on said outside surface, a second recess axially aligned with said first recess forming a second open-ended chamber on said inside surface, and a connecting aperture extending between said first and second open-ended chambers;

means comprising an electrically conductive terminal having a first portion adapted to receive a connecting terminal in said first chamber, and a second portion including a contact surface in said second chamber, said first and second portions being connected through said connecting aperture;

means comprising a sponge-like contact member saturated with electrically conductive fluid disposed within said second chamber in contact with said contact and dimensioned to extend through the open end thereof;

a disc-shaped cover member having an inside surface substantially coextensive with said inside surface of said base member, said cover member being, overall, substantially less flexible than said flange portion of said base member and including a thumb recess along its circumference at said inside surface to facilitate peeling said base member away therefrom; and an adhesive layer on the inside surface of said base member retaining said inside surface of said cover member against said inside surface of said base member so as to enclose said contact member within said second open-ended chamber and increase the rigidity of said electrode assembly during storage, said base member being peelable away from said cover member to expose said layer of adhesive for contact with the underlying skin surface to hold said sponge-like contact member in contact with the skin surface while the electrode assembly is in use.

4. In a disposable electrode assembly for establishing an electrical connection with an underlying skin surface, said electrode assembly comprising a relatively flexible base member formed of electrically-insulating material defining an outside surface and an adhesive carrying inside surface, said base member carrying an electrically conductive terminal on said inside surface and adapted for holding said terminal in contact with the skin surface, said terminal communicating with said outside surface, and a cover member being, overall, substantially less flexible than the major extent of said base member, said cover member having an inside surface attached to and being substantially coextensive with said adhesive carrying surface so as to enclose said terminal and increase the rigidity of said electrode assembly during storage, the improvement wherein said cover member includes a thumb recess about its margin at the inside surface to facilitate peeling said base member away from said cover member to enable said adhesive carrying inside surface to be placed in contact with the underlying skin surface to hold the electrically conductive terminal in contact with the skin while the electrode assembly is in use.

5. In a disposable electrode assembly for establishing an electrical connection with an underlying skin surface, said electrode assembly comprising a relatively flexible base member formed of electrically-insulating material defining an outside surface and an adhesive carrying inside surface having an open-ended chamber thereon, said base member containing within said chamber a sponge-like electrical contact member projecting outwardly in an expanded state beyond said adhesive carrying surface, said contact member having a portion communicating with the outside surface, and a cover member being, overall, substantially less flexible than the major extent of said base member, said cover member having an inside surface attached to and being substantially coextensive with said adhesive carrying surface so as to enclose said sponge-like contact member in a compressed state within said chamber and increase the rigidity of individual ones of said electrode assemblies during storage, the improvement wherein said cover member includes a thumb recess about its margin at said inside surface to facilitate peeling said base member away from said cover member to enable said adhesive carrying inside surface to be placed in contact with the underlying skin surface to hold the sponge-like contact member in contact with the skin while the electrode assembly is in use.

* * * * *